United States Patent
Oh et al.

(10) Patent No.: US 11,476,012 B2
(45) Date of Patent: Oct. 18, 2022

(54) APPARATUS OF PRODUCING NUCLIDE USING FLUID TARGET

(71) Applicant: KOREA INSTITUTE OF RADIOLOGICAL & MEDICAL SCIENCES, Seoul (KR)

(72) Inventors: Se Young Oh, Seoul (KR); Sang Moo Lim, Seoul (KR); Kyo Chul Lee, Seoul (KR); Joo Hyun Kang, Seoul (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 214 days.

(21) Appl. No.: 16/917,316

(22) Filed: Jun. 30, 2020

(65) Prior Publication Data
US 2021/0027904 A1 Jan. 28, 2021

(30) Foreign Application Priority Data
Jul. 25, 2019 (KR) .......................... 10-2019-0090463

(51) Int. Cl.
| | |
|---|---|
| *G21G 1/00* | (2006.01) |
| *G21G 1/10* | (2006.01) |
| *H05H 6/00* | (2006.01) |
| *A61K 51/12* | (2006.01) |

(52) U.S. Cl.
CPC .............. *G21G 1/10* (2013.01); *A61K 51/121* (2013.01); *H05H 6/00* (2013.01); *A61K 2121/00* (2013.01); *G21G 2001/0089* (2013.01)

(58) Field of Classification Search
CPC ... G21G 1/10; G21G 1/001; G21G 2001/0089
See application file for complete search history.

(56) References Cited

U.S. PATENT DOCUMENTS

| | | |
|---|---|---|
| 5,770,030 A | 6/1998 | Hamacher et al. |
| 2002/0094056 A1 | 7/2002 | Satz et al. |
| 2003/0007588 A1* | 1/2003 | Kiselev ................... G21G 1/10 |
| | | 376/195 |

(Continued)

FOREIGN PATENT DOCUMENTS

| | | |
|---|---|---|
| EP | 0752709 A1 | 1/1997 |
| EP | 0962942 A1 | 12/1999 |

(Continued)

OTHER PUBLICATIONS

"Development of Actinium-225 Production Method using Liquid Targe", 11th International Symposium on Targeted Alpha Therapy, Proceedings from the TAT11/Journal of Medical Imaging and Radiation Sciences 50 (2019) S1-S42, Apr. 1, 2019, 25 pages, Fairmont Château Laurier, Ottawa, ON Canada.

*Primary Examiner* — Sharon M Davis (57) ABSTRACT

The disclosure provide an apparatus for producing a nuclide by using a liquid target which can perform the nuclear reaction process and can discharge the radioactive gas such as Radon within the vial. As described above, an apparatus for producing a nuclide by using a liquid target according to the present disclosure can minimize quantitative loss of a reactant by performing the nuclear reaction process using a target of a liquefied state and reusing a liquefied target on which the nuclear reaction process has not been performed, and can improve safety by enabling the radioactive gas generated to be disposed.

10 Claims, 11 Drawing Sheets

(56) References Cited

U.S. PATENT DOCUMENTS

| | | | |
|---|---|---|---|
| 2003/0127395 A1* | 7/2003 | Bond | G21G 4/08 |
| | | | 423/11 |
| 2007/0297554 A1 | 12/2007 | Lavie et al. | |
| 2009/0191122 A1 | 7/2009 | Moreno Bermudez et al. | |
| 2015/0170775 A1* | 6/2015 | Nutt | G21K 5/08 |
| | | | 376/202 |
| 2018/0350480 A1* | 12/2018 | Torgue | B01D 15/362 |

FOREIGN PATENT DOCUMENTS

| | | |
|---|---|---|
| EP | 0962942 B1 | 4/2003 |
| EP | 1599882 B1 | 12/2006 |
| JP | 37328568 B | 1/2006 |
| JP | 2007508531 A | 4/2007 |
| JP | 2007536533 A | 12/2007 |
| JP | 2009047668 A | 3/2009 |
| JP | 2009527731 A | 7/2009 |
| JP | 5145545 B2 | 2/2013 |
| JP | 2017178865 A | 10/2017 |
| JP | 2018190711 A | 11/2018 |
| WO | 03/081604 A1 | 10/2003 |
| WO | 2019008665 A1 | 1/2019 |
| WO | WO-2020260210 A1 * | 12/2020 ............... G21G 1/10 |

* cited by examiner

APPARATUS OF PRODUCING NUCLIDE USING FLUID TARGET

CROSS-REFERENCE TO RELATED APPLICATIONS

Priority to Korean patent application number 10-2019-0090463 filed on Jul. 25, 2019 the entire disclosure of which is incorporated by reference herein, is claimed.

FIELD OF THE INVENTION

The present disclosure relates to an apparatus for producing a nuclide by using a liquid target and, more specifically, to an apparatus for producing a nuclide by using a liquid target, the apparatus capable of disposing a radioactive gas generated when producing a nuclide by using a liquefied target.

BACKGROUND OF THE INVENTION

Ac-225 is produced while two neutrons are escaping from the radium-226 target material when accelerating and colliding a proton with a radium-226 target material by a nuclear reaction of 226Ra(p, 2n)225Ac to produce actinium-225, i.e., a radioactive medicine for treatment. A Ra-226 material used at this time generally includes a powder-type target among solid targets. A Ra-226 powder to which the proton has been irradiated passes through a series of separation and purification processes in order to separate Ac-225 which is included in the powder and has been produced by performing a nuclear reaction. To this end, a method of producing Ac-225 may comprise melting Ra-226 into a liquefied form, passing a liquefied Ra-226 through separation and purification processes, and performing a process of preparing the powder type Ra-226 to reuse a powder type Ra-226 for producing Ac-225 again. A method of producing Ac-225 by using such a powder type Ra-226 is disclosed in U.S. Pat. No. 6,680,993.

However, such a conventional technique makes a quantitative loss of Ra-226 according as Ra-226 is changed into a powder form and a liquefied form in a series of processes for producing Ac-225. Due to problems that Ra-226 has a long half-life of about 1,600 years at present, and releases radon, i.e., an inert gas in the decay process, there have been difficulties in disposal and storage of Ra-226, and, for this reason, additional production has been suspended. Therefore, it is desirable that a loss of Ra-226 is minimized in the process of producing Ac-225 by using Ra-226 which has not been left much in the world. Further, since radon generated from Ra-226 when producing Ac-225 using Ra-226 is also a radioactive material, the need that radon should be safely disposed arises.

SUMMARY OF THE INVENTION

The purpose of the present disclosure is to provide an apparatus for producing a nuclide by using a liquid target, the apparatus which minimizes loss of Ra-226 that may be generated in the process of producing Ac-225 by performing a nuclear reaction using conventional Ra-226, and which is capable of safely disposing radon generated from Ra-226.

To achieve the purpose, the present disclosure may provide an apparatus for producing a nuclide by using a liquid target, the apparatus including a chamber provided with a reaction space which is configured to accommodate a liquid reactant, a vial which is configured to temporarily accommodate the liquid reactant before a nuclear reaction process and a liquid product after the nuclear reaction process, a syringe pump which is driven to suck a liquid material accommodated in the vial before the nuclear reaction process and enable the sucked liquid material to be supplied to the chamber, and an exhaust unit which is formed such that a radioactive gas within the vial can be discharged.

Here, the liquid reactant comprises liquefied radium (Ra-226), the liquid product comprises liquefied radium (Ra-226) and liquefied actinium (Ac-225), and the radioactive gas may be radon (Rn).

Meanwhile, an apparatus for producing a nuclide by using a liquid target according to the present disclosure may additionally include a first shielding box which accommodates the vial in an inner space thereof to prevent leakage of the radioactive gas to the outside when the radioactive gas is flown out of the vial.

On the other hand, an apparatus for producing a nuclide by using a liquid target according to the present disclosure may additionally include a second shielding box which is configured to accommodate the syringe pump and the first shielding box in an inner space thereof and enable leakage of the radioactive gas to the outside to be prevented.

Further, an apparatus for producing a nuclide by using a liquid target according to the present disclosure may additionally include a first flow path which includes a branch part such that an end of the branch part can be connected to each of a lower side of the chamber, the vial, and the syringe pump, and a first 3-way valve which is provided in the branch part of the first flow path and is configured to enable a transfer path of fluid in the first flow path to be selected.

Meanwhile, an apparatus for producing a nuclide by using a liquid target according to the present disclosure may additionally include an inert gas source which supplies an inert gas such that the liquid product can be transferred.

Further, an apparatus for producing a nuclide by using a liquid target according to the present disclosure may additionally include a second flow path which includes a branch part such that an end of the branch part can be connected to each of an upper side of the chamber, the vial, and the inert gas source, and a second 3-way valve which is provided in the branch part of the second flow path and is configured to enable a transfer path of fluid in the second flow path to be selected.

Further, the branch part of the first flow path, the first 3-way valve, the branch part of the second flow path, and the second 3-way valve may be disposed inside the second shielding box.

Meanwhile, an apparatus for producing a nuclide by using a liquid target according to the present disclosure may additionally include a first shielding pipe which is configured to be able to shield a portion of the first flow path positioned between the second shielding box and the chamber and a second shielding pipe which is configured to be able to shield a portion of the second flow path positioned between the second shielding box and the chamber.

Meanwhile, when loading the liquid reactant into the chamber, opening direction of the first 3-way valve is adjusted such that the syringe pump in the first flow path can be communicated with a lower side of the chamber, and opening direction of the second 3-way valve may be adjusted such that the gas can be discharged to the exhaust unit after gas inside the first flow path, the reaction space within the chamber, and the second flow path is moved to the vial according as the liquid reactant is transferred to the chamber.

Further, when unloading the liquid product after a nuclear reaction process, opening direction of the second 3-way valve is adjusted such that an inert gas can be blown into the chamber from the inert gas source, and gas within the vial may be discharged to the exhaust unit according as the liquid product is transferred to the vial.

Further, the exhaust unit may additionally include a radon collection part which collects radon gas from an exhausted gas.

On the other hand, the exhaust unit additionally includes a radon gas storage part which stores the radon gas and may be configured to store radon during at least one cycle of a half-life.

Further, an apparatus for producing a nuclide by using a liquid target according to the present disclosure may additionally include a separating and refining unit which is configured to be able to separate and refine the liquid product, and pure liquefied radium separated from the separating and refining unit is recovered into the vial such that the recovered pure liquefied radium can be reused in the nuclear reaction process.

An apparatus for producing a nuclide by using a liquid target according to the present disclosure can minimize quantitative loss of a reactant by performing the nuclear reaction process using a target of a liquefied state and reusing a liquefied target on which the nuclear reaction process has not been performed, and can improve safety by enabling the radioactive gas generated to be disposed.

DESCRIPTION OF EXEMPLARY EMBODIMENTS

Hereinafter, an apparatus for producing a nuclide by using a liquid target according to an embodiment of the present disclosure will be described in detail with reference to the accompanying drawings. Names of respective elements in the description of the following embodiments can be referred to as other names in the art. However, if there are functional similarities and identities in the elements, the elements can be said to have equivalent configurations although modified embodiments are adopted. Further, marks added to the respective elements are described for convenience of explanation. However, illustration contents on drawings having these marks described thereon do not limit the respective elements to the scope within the drawings. Similarly, if there are functional similarities and identities in the elements although partially modified embodiments adopt configurations on the drawings, the elements can be said to have equivalent configurations. Further, when the elements are recognized as elements which should be naturally included by looking at a general technician level of the field of the art, the explanations thereof are omitted.

Meanwhile, it is explained on the premise hereinafter that the liquid target may become liquefied radium, and a p, 2n nuclear reaction occurs in Ra-226 of a liquefied state, and Ac-225 of a liquefied state is produced when a particle beam is irradiated to the liquefied radium. Further, it is explained on the premise hereinafter that a product is a state in which Ra-226 of a liquid state and Ac-225 are mixed. Further, it is explained on the premise that a radioactive gas is a radon gas which is consistently generated as Ra-226 is decayed. However, the present disclosure is not limited thereto, but may target on a nuclide from which the radioactive gas is generated before a nuclear reaction process, after the nuclear reaction process, or consistently. Further, although radium chloride ($RaCl_2$) as the liquefied radium and actinium chloride ($AcCl_3$) as liquefied actinium have been described with illustration, this is an example only, and radium liquefied using various organic liquids may be used.

Figure 1:
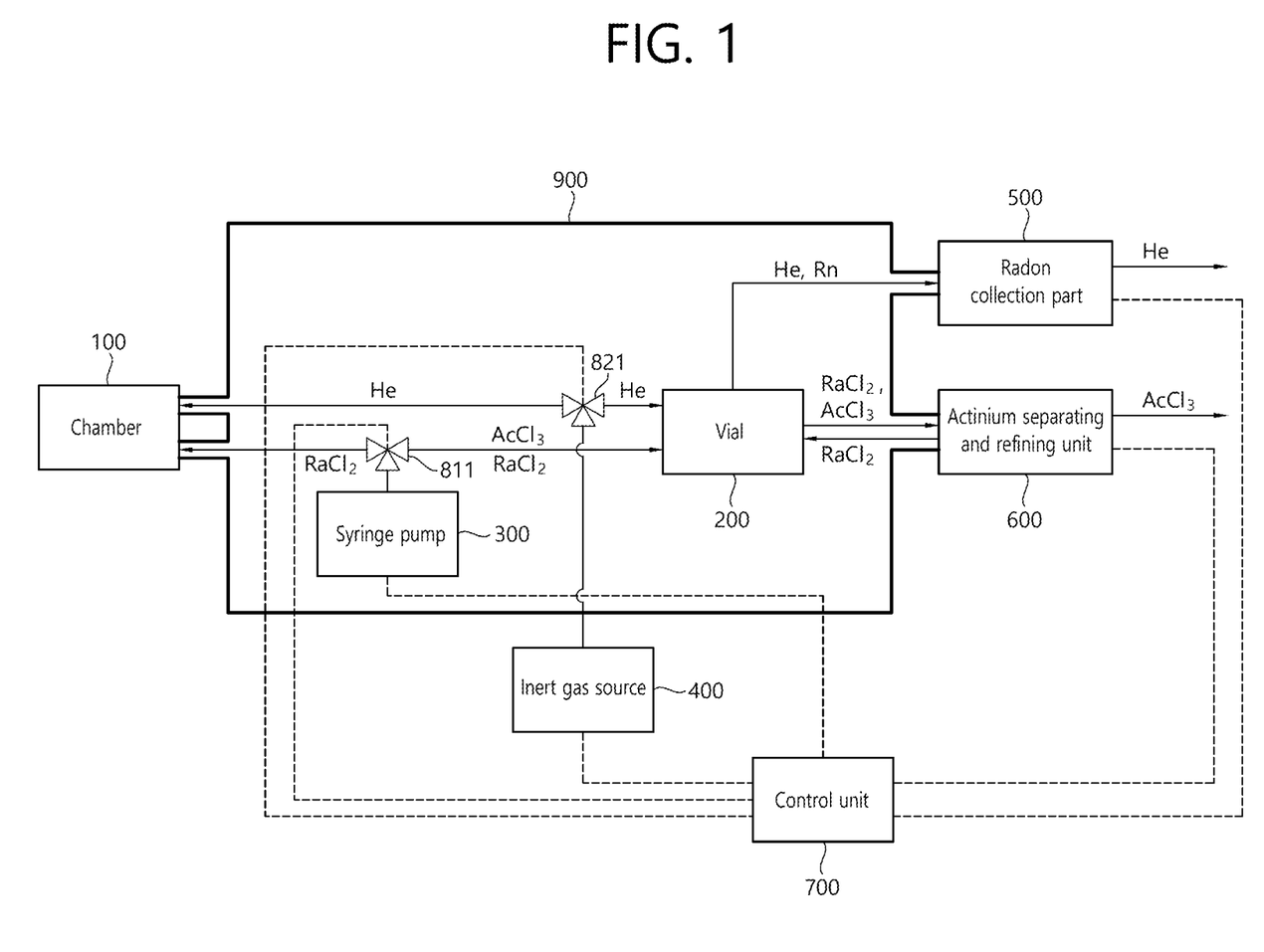
FIG. 1 is a block diagram of an apparatus for producing a nuclide by using a liquid target, i.e., an embodiment according to the present disclosure.

FIG. 1 is a block diagram of an apparatus for producing a nuclide by using a liquid target, i.e., an embodiment according to the present disclosure. Concepts and connection relations of respective elements according to the present disclosure are described with reference to the present drawing, and operations of the respective elements will be described later in detail with reference to FIG. 2 to FIG. 9.

As illustrated in FIG. 1, an apparatus for producing a nuclide by using a liquid target according to the present disclosure may include a chamber 100, a vial 200, a syringe pump 300, a helium source 400, an exhaust unit, an actinium separating and refining unit 600, a control unit 700, and a radioactive gas shielding unit 900.

The chamber 100 is constructed to provide a reaction space in which a nuclear reaction process can be performed. The chamber 100 has the reaction space provided in an inner side thereof such that the reaction space can accommodate the liquid target, and a flow path for flowing out or flowing in the liquid target may be formed in the chamber 100. Further, a window 101 which is formed in the form of a foil 101 such that an internal environment of the reaction space is isolated from the outside may be provided in one side of the chamber 100 to which a particle beam is irradiated. The reaction space of the chamber 100 may be formed such that the reaction space is in fluid communication with each of a first flow path 810 and a second flow path 820 which will be described later, the liquid target can exit or enter the reaction space, and an inert gas can flow in the reaction space or flow out of the reaction space.

On the other hand, although it has not been described above, a beam line connected to the chamber 100 may be maintained in a vacuum state, and the chamber 100 may be isolated from the beam line such that a liquefied target can be moved independently from the beam line in the reaction space 110 within the chamber 100. The chamber 100 includes a foil 101 which is formed of a metallic material in an irradiation path of a particle beam 10 to isolate the chamber 100 from the beam line, and the foil 101 may be configured to seal each of the beam line and the chamber 100. Meanwhile, since heat is generated when the particle beam 10 is irradiated if the foil 101 seals respective opening portions of the beam line and the chamber 100 in a connection part of the beam line and the chamber 100, a separate cooling unit for cooling the connection part of the beam line and the chamber 100 may be provided. Further, an apparatus for producing a nuclide by using a liquid target according to the present disclosure may include a water cooling-type cooling line for cooling the liquid target while a nuclear reaction process is being performed in the reaction space having the liquid target accommodated therein. However, since such a cooling line is a configuration which is widely used in an apparatus for producing a nuclide by using a general liquid target, a more detailed description thereof will be omitted.

The vial 200 is a space for temporarily loading a liquefied target and a product which is produced after performing a nuclear reaction process. The liquid target may be moved from the vial 200 to the chamber 100 through the syringe pump 300. After the nuclear reaction process is performed in the chamber 100, the product is moved to the vial 200. Further, the vial 200 may be connected to be in fluid communication with the separating and refinement unit which is constructed to be able to separate the product into liquefied radium and liquefied actinium. Further, an opening portion may be formed in the vial 200 such that gas can be discharged through the opening portion while pressure inside the vial is being maintained during loading or unloading of the liquid target.

The syringe pump 300 is configured to be able to extrude the liquefied radium after sucking a predetermined amount of liquefied radium accommodated within the vial 200. The extruded liquefied radium can be transferred to the reaction space of the chamber 100.

An inert gas source 400 is configured to be able to generate a driving force which can flow fluid of an apparatus for producing a nuclide by using a liquid target. The inert gas source 400 may include a high stability gas which is not reacted with the liquid target or a radioactive gas generated therefrom. For example, an inert gas may be helium (He). The helium source 400 may be configured to move liquid or discharge gas inside the vial 200 to the outside by blowing helium into a flow path.

The exhaust unit is configured to be able to discharge a radon gas consistently generated from radium. Although the exhaust unit does not include a separate element for movement, the exhaust unit is configured to be able to discharge gas by a pressure difference generated according as liquefied radium or liquefied product is moved. The exhaust unit may include a gas discharge flow path 830 of which one side is connected to the first shielding box, and which is provided by passing through the second shielding box, and a radon collection part 500. Further, the exhaust unit may include a radon storage unit instead of the radon collection part 500.

The radon collection part 500 is configured to perform a preparation process for disposing collected radon. The radon collection part 500 is configured such that gas discharged from the vial 200 can be flown in the radon collection part 500. The radon collection part 500 is configured to condense radon gas only and pass remaining gas in an extremely low temperature environment. The condensed radon may be discarded as radioactive waste. Meanwhile, when the exhaust unit includes the radon storage unit, the radon storage unit unlike the radon collection part may discharge radon after securing stability after storing radon in the radon storage unit until radon goes through a sufficient half-life, or may discharge the diluted radon to the outside after diluting radon with a sufficient amount of air.

The actinium separating and refining unit 600 is configured to be able to separate actinium from a liquid product and refine the separated actinium. The actinium separating and refining unit 600 may be a separate space, e.g., a space such as a glove box or hot-cell, and enables a user to perform separation and refinement of actinium through an appropriate process. The actinium separating and refining unit 600 may be configured such that the recovered pure liquefied radium can be transferred to the vial 200 by recovering pure liquefied radium again after separating actinium from the liquid product. The recovered pure liquefied radium can be reused in a nuclear reaction process after passing through the refinement process.

The control unit 700 is configured to be able to control overall operation of an apparatus for producing a nuclide by using a liquid target. The control unit 700 enables the syringe pump 300, the helium source 400 and others to be operated to preset values according to input or by the user. Further, the control unit 700 can generate a control input such that the control unit 700 can control operation of a valve which will be described later. Further, it has not been illustrated, the control unit 700 is configured to be able to perform a monitoring process in a state that the control unit 700 is connected sensors which are capable of measuring states of pressure, temperature and others at a plurality of points. However, since such a configuration of the control unit 700 may be modified and applied in various manners, a detailed description of the configuration will be omitted.

The radioactive gas shielding unit 900 is configured to isolate a path for transferring liquefied radium and a space for flowing radon gas from the outside. The radioactive gas shielding unit 900 isolates a predetermined zone to prevent contamination of an external space although radon gas is flown out from a flow space. The radioactive gas shielding unit 900 may include a first shielding box 910, a second shielding box 920, a first shielding pipe 930, and a second shielding pipe 940. Meanwhile, specific configuration of such a radioactive gas shielding unit 900 will be described below in detail with reference to FIG. 2.

Figure 2:
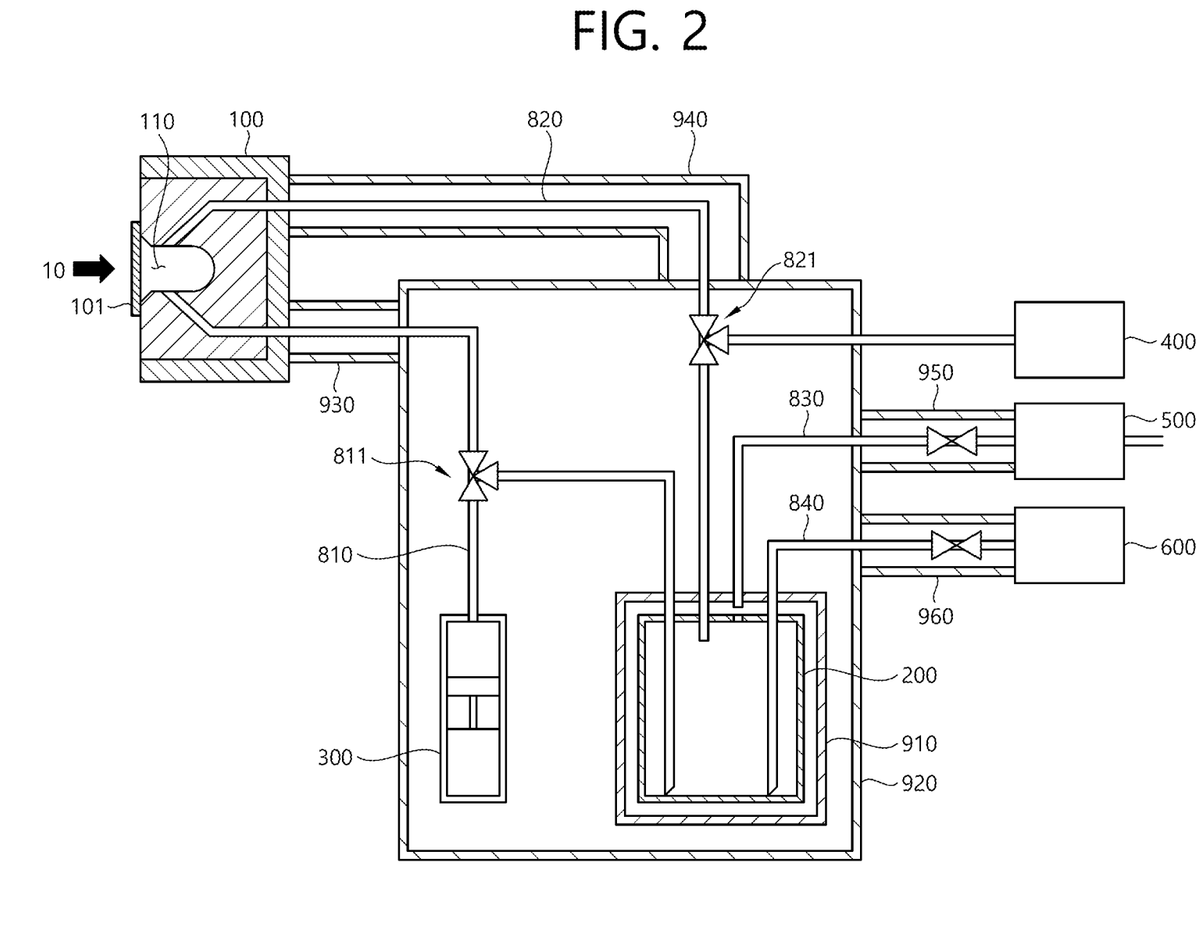
FIG. 2 is a conceptual diagram of an apparatus for producing a nuclide by using a liquid target, i.e., an embodiment according to the present disclosure.

FIG. 2 is a conceptual diagram of an apparatus for producing a nuclide by using a liquid target, i.e., an embodiment according to the present disclosure. A flow path and the radioactive gas shielding unit 900 will be described in detail with reference to the present drawing.

Firstly, when examining the flow path, the flow path may include a first flow path 810, a second flow path 820, a gas discharge flow path 830, and a product transfer flow path 840.

The first flow path 810 may be configured such that the first flow path 810 can connect lower sides of the vial 200, syringe pump 300 and chamber 100, and includes a branch portion such that the aforementioned vial 200, syringe pump 300 and chamber 100 are in fluid communication with one another. A first 3-way valve 811 may be provided in the branch portion of the first flow path 810 such that a fluid transfer path among three flow paths connected to the branch portion of the first flow path 810 can be selectively opened or closed.

The second flow path 820 may be configured such that the second flow path 820 can be connected to upper sides of the vial 200, helium source 400 and chamber 100, and includes a branch portion such that the upper sides of the aforementioned vial 200, helium source 400 and chamber 100 are in fluid communication with one another. A second 3-way valve 821 may be provided in the branch portion of the second flow path 820 such that a fluid transfer path among three flow paths connected to the branch portion of the second flow path 820 can be selectively opened or closed.

The gas discharge flow path 830 is configured such that gas can be transferred by connecting one side of the first shielding box 910 which will be described later to the radon collection part 500.

The product transfer flow path 840 is configured by connecting the vial 200 to the actinium separating and refining unit.

The radioactive gas shielding unit 900 is configured to be able to prevent production facilities from being entirely contaminated although a radioactive material is flown out. The radioactive gas shielding unit 900 may include a first shielding box 910, a second shielding box 920, a first shielding pipe 930, a second shielding pipe 940, a third shielding pipe 950, and a fourth shielding pipe 960.

The first shielding box 910 is configured to primarily shield the vial 200 at the outside of the vial 200. Meanwhile, the vial 200 is configured to allow a space inside a shielding box and a space inside the vial 200 to be in fluid communication with each other by forming an opening portion in one side thereof, and the vial 200 may be configured such that gas which has been contained inside the vial 200 can be naturally moved to the outside of the vial 200 when pressure within the vial 200 is increased. The opening portion of the vial 200 is preferably formed in an upper side of the vial 200 such that only gas can be flown out to the outside.

The second shielding box 920 is configured to be able to doubly shield the radon gas with respect to a zone having a relatively high risk of flowing out radon gas. The second shielding box 920 is configured to be able to accommodate the first shielding box 910, syringe pump 300, first 3-way valve 811 and second 3-way valve 821 in an inner side thereof.

The aforementioned first shielding box 910 and second shielding box 920 may be formed of material having sufficient shielding power such that radiation cannot reach an outer portion of the first shielding box 910 or second shielding box 920 although the radon gas is flown out of a normal flow path.

On the other hand, the first flow path 810, second flow path 820, gas discharge flow path 830 and product transfer flow path 840 can connect elements inside and outside the shielding boxes by passing through the first shielding box 910 and second shielding box 920. Portions where the respective flow paths pass through the shielding boxes can be perfectly sealed and fixed.

A plurality of shielding pipes 930, 940, 950 and 960 are configured such that the plurality of shielding pipes 930, 940, 950 and 960 can be shielded from the outside while covering flow paths disposed in outer portions of the shielding boxes 910 and 920. The first shielding pipe 930 is configured to be able to shield a portion of the first flow path 810 disposed in an outer portion of the second shielding box 920. The second shielding pipe 940 is configured to be able to shield a portion of the second flow path 820 disposed in an outer portion of the second shielding box 920. The third shielding pipe 950 is configured to be able to shield the gas discharge flow path 830 disposed in an outer portion of the second shielding box 920. The fourth shielding pipe 960 is configured to be able to shield the product transfer flow path 840 disposed in an outer portion of the second shielding box 920.

Hereinafter, operation of an apparatus for producing nuclide according to the present disclosure will be described in detail with reference to FIG. 3 to FIG. 9.

Figure 3:
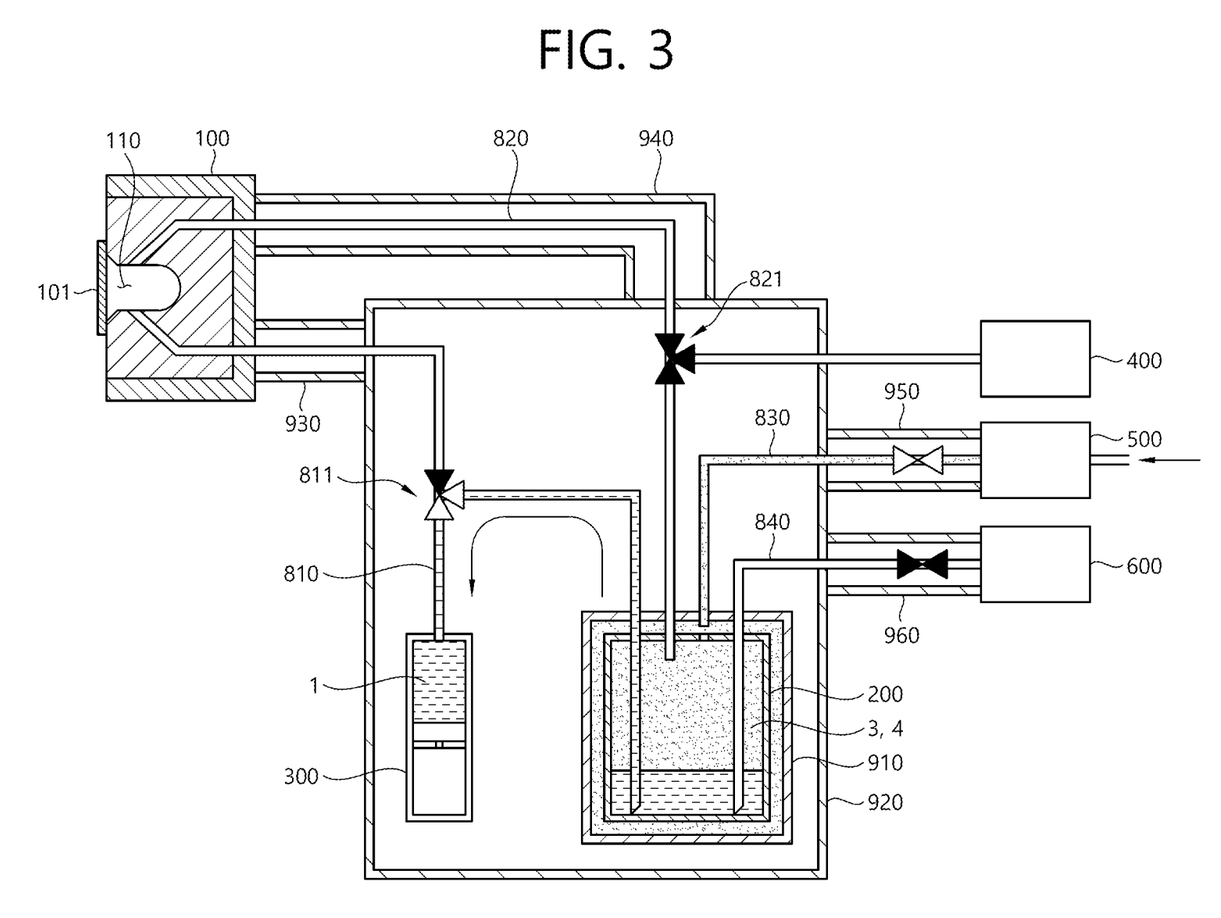
FIG. 3 is a conceptual diagram illustrating a loading process.
Figure 4:
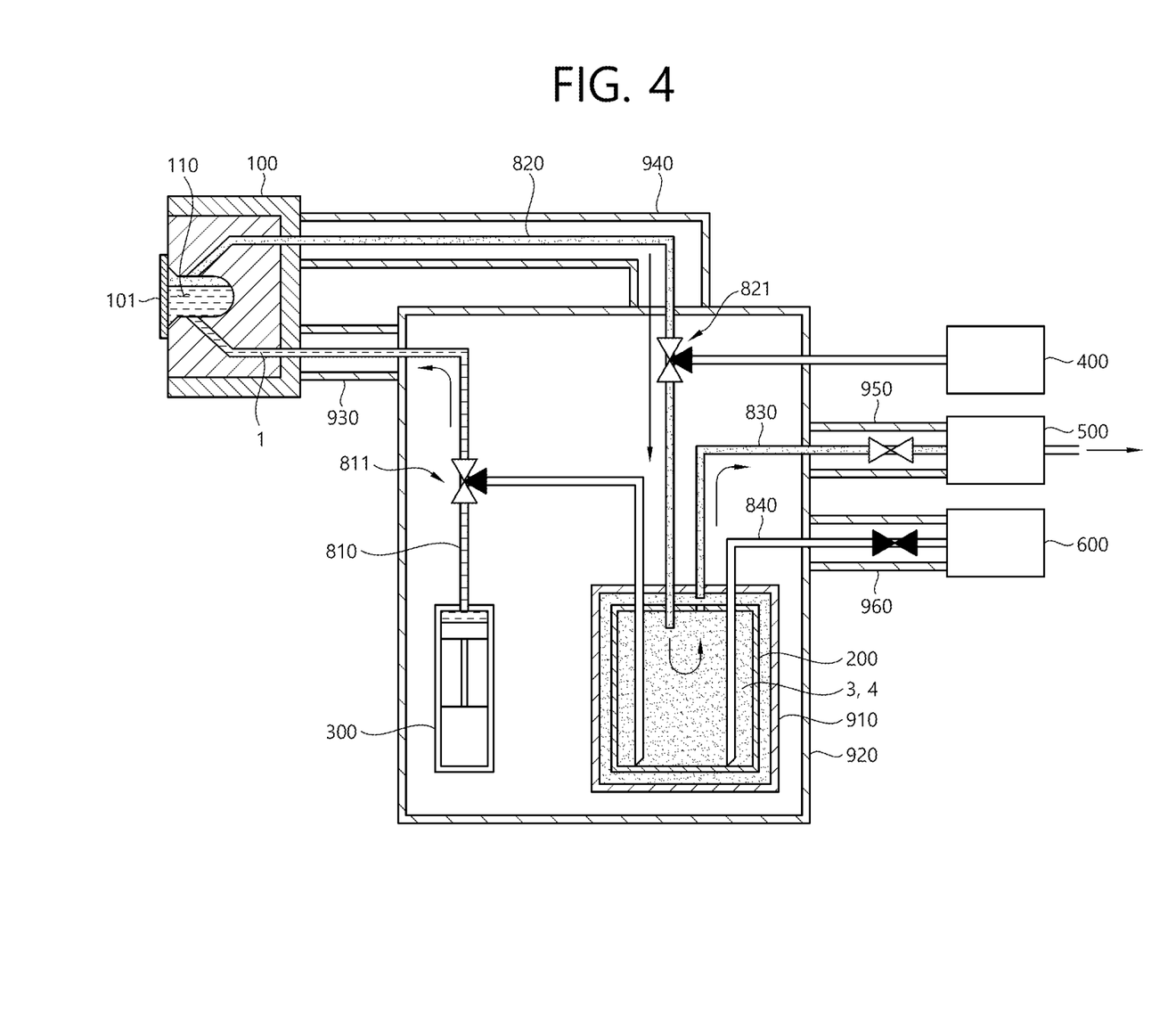
FIG. 4 is the other conceptual diagram illustrating the loading process.

FIG. 3 and FIG. 4 are conceptual diagrams illustrating the loading process.

As illustrated in FIG. 3, a syringe pump 300 accommodates the liquefied radium 1 by sucking liquefied radium 1 accommodated in a vial 200 during a loading process as much as a fixed quantity. At this time, the quantity of the liquefied radium 1 sucked into the syringe pump 300 may also be determined by considering a quantity of the liquefied radium 1 accommodated in a chamber 100 and a quantity of the liquefied radium 1 which is stagnant in a flow path from the syringe pump 300 to the chamber 100. As illustrated in FIG. 4, when the syringe pump 300 extrudes the liquefied radium 1, the liquefied radium 1 is moved along the flow path, and then is loaded in the chamber 100. Further, according as the liquefied radium 1 is accommodated in the chamber 100, gas including radon is moved to the vial through an upper flow path in FIG. 4, and is discharged through a flow path provided in one side of the vial such that the gas including radon passes through a radon collection part 500.

Figure 5:
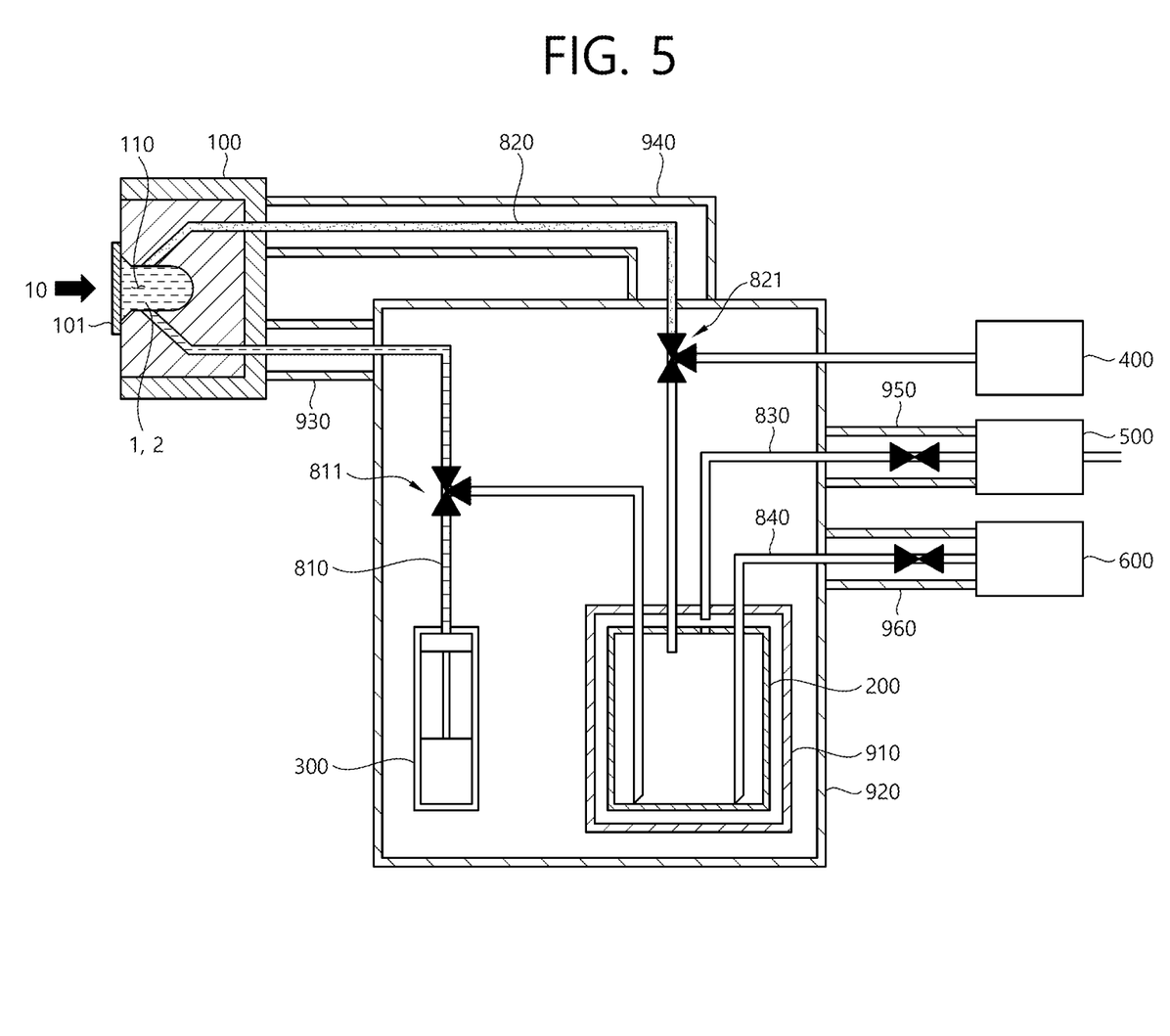
FIG. 5 is a conceptual diagram illustrating a nuclear reaction process.

FIG. 5 is a conceptual diagram illustrating a nuclear reaction process. As a preparation process, a valve between the syringe pump 300 and the chamber 100 may be closed in order to prevent movement of the liquefied radium 1 when the liquefied radium 1 is loaded in the chamber 100. Further, a valve between the chamber 100 and a helium source 400 may be closed to prevent backflow of a radioactive material due to pressure increased during a nuclear reaction process. Thereafter, the nuclear reaction process is performed by irradiating a particle beam to a reaction space 110. Meanwhile, pressure within the reaction space 110 may be maintained as the helium source is operated when the valve between the helium source 400 and the chamber 100 is opened.

Figure 6:
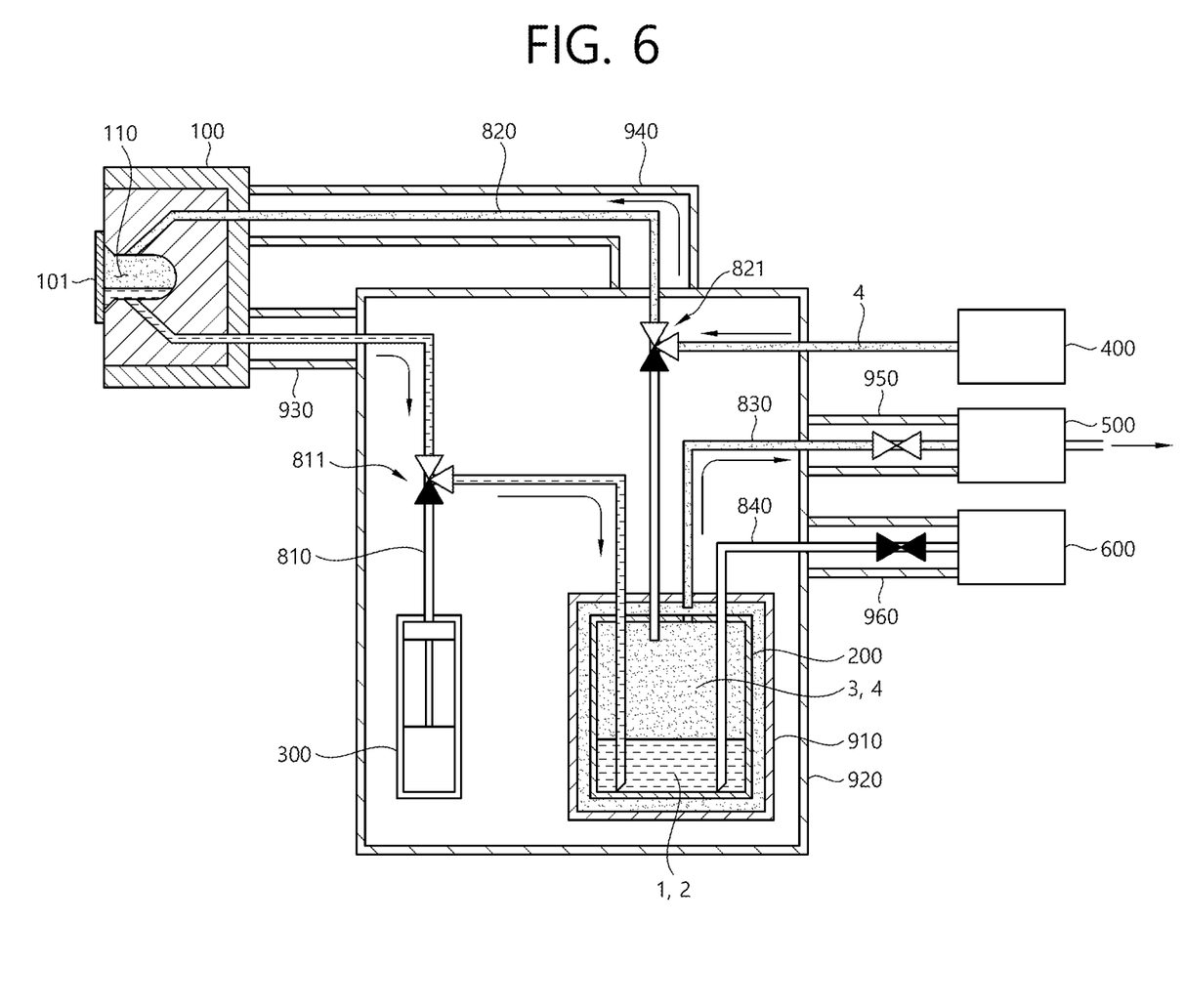
FIG. 6 is a conceptual diagram illustrating an unloading process.

FIG. 6 is a conceptual diagram illustrating an unloading process.

During an unloading process, a valve is operated to open a flow path facing the vial 200 from the reaction space 110, and a product is moved to the vial 200 by blowing a helium gas 4 into the reaction space 110. At this time, it is preferable to blow a sufficient amount of helium into the reaction space 110 such that the product is not remained in the reaction space 110 and the flow path from the reaction space 110 to the vial 200. On the other hand, the helium gas 4 is flown in the reaction space 110 through a second flow path 820 connected to an upper side of the reaction space 110, and liquefied radium 1 may be moved through a first flow path 810 connected to a lower side of the reaction space 110. Therefore, a product of a liquefied state may be naturally discharged to the outside of the chamber 100 from the lower side of the reaction space 110 when blowing the helium gas 4 into the reaction space 110.

Figure 7:
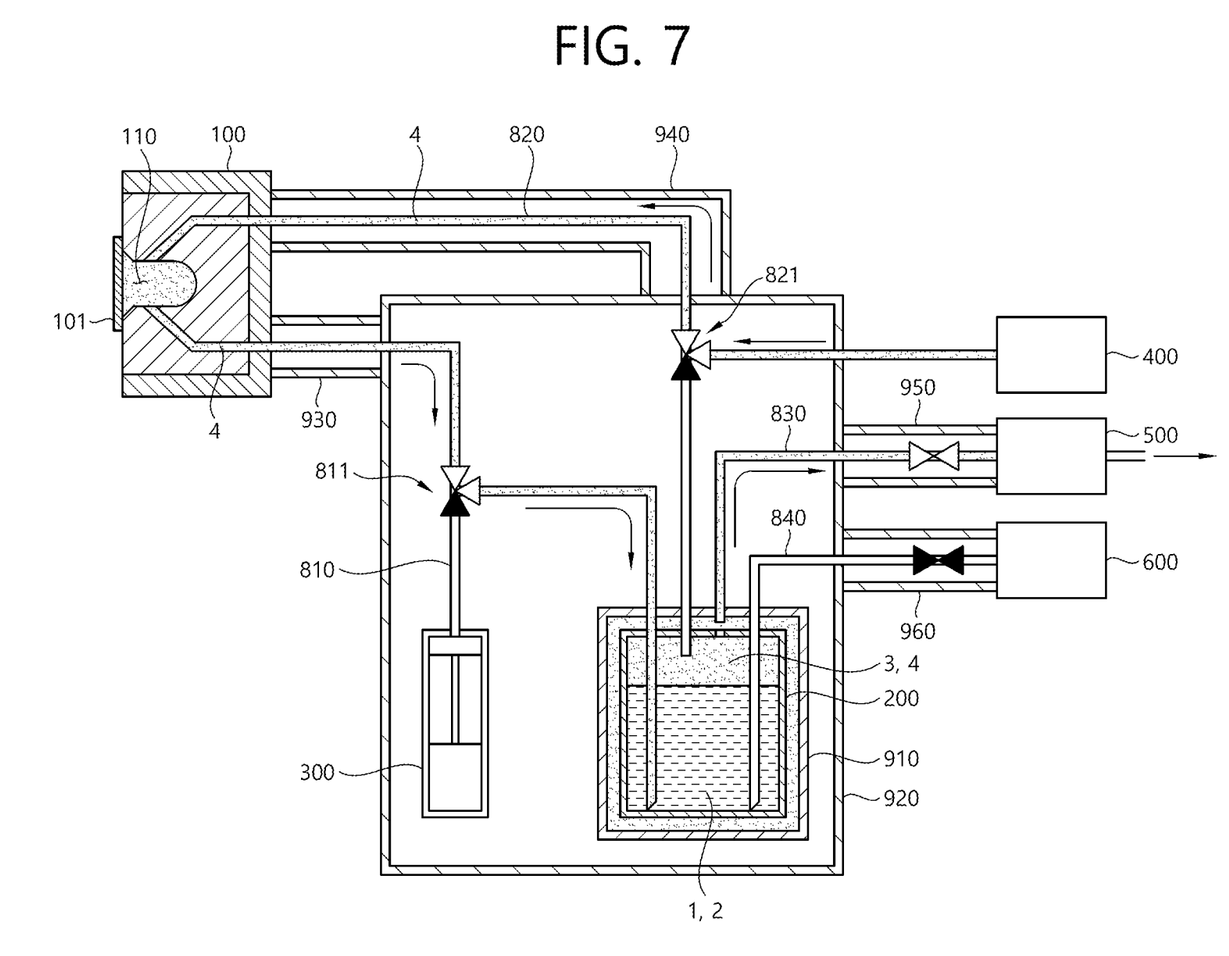
FIG. 7 is a conceptual diagram illustrating a process of discharging radon in the unloading process.

FIG. 7 is a conceptual diagram illustrating a process of discharging radon in the unloading process.

As illustrated in FIG. 7, according as a liquefied product is flown in a vial 200 while performing an unloading step, gas within the vial 200 is discharged along a gas discharge flow path 830 such that the gas passes through a radon collection part 500. Thereafter, the radon collection part 500 discharges remaining gas to the outside after collecting the gas of radon 3 only from a gas in which a helium gas 4 is mixed together with gas of radon 3. As described above, the collected radon can be disposed as a radioactive waste in a liquefied state when radon is collected. Further, although it has not been illustrated in FIG. 7, when the radon collection part 500 is not provided, radon is stored for a predetermined time, or is diluted with a sufficient amount of air to enable the diluted radon to be discharged to the outside.

Figure 8:
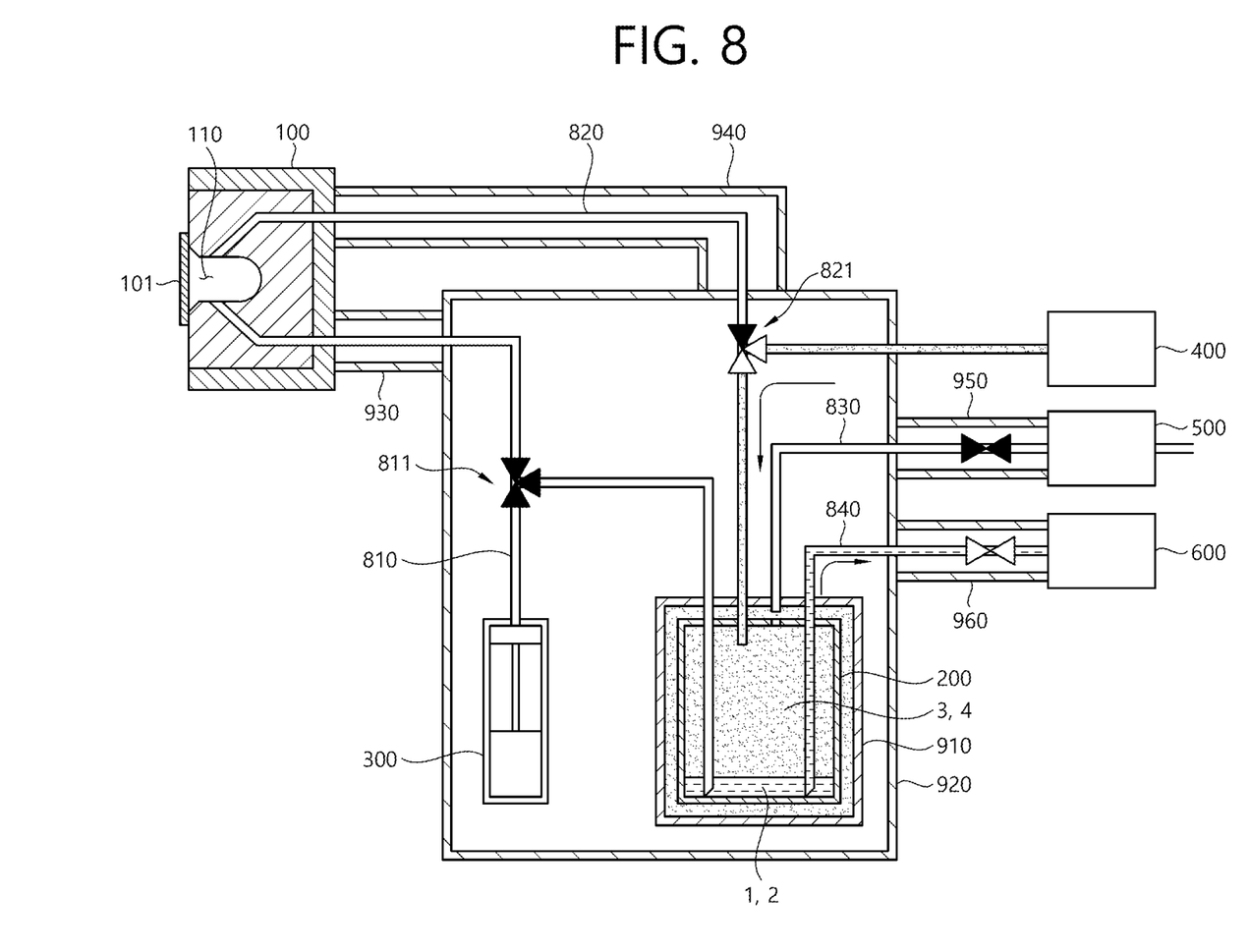
FIG. 8 is a conceptual diagram illustrating a step of moving a product to separate and refine actinium.

FIG. 8 is a conceptual diagram illustrating a step of transferring a liquefied product to separate and refine actinium.

As illustrated in FIG. 8, the liquefied product is transferred from the vial to a space for refinement and separation to separate and refine actinium. Specifically, the product is transferred to the actinium separating and refining unit 600 by opening a valve provided in a product transfer flow path 840 provided between a vial 200 and an actinium separating and refining unit 600 and blowing a helium gas 4 into the vial 200. Liquefied radium 1 and liquefied actinium 2 may be separated from each other in the actinium separating and refining unit 600. Refinement of actinium comprises performing an appropriate refinement process comprising removing impurities from the separated actinium such that the separated actinium can be used for medical purposes after transferring separated actinium.

Figure 9:
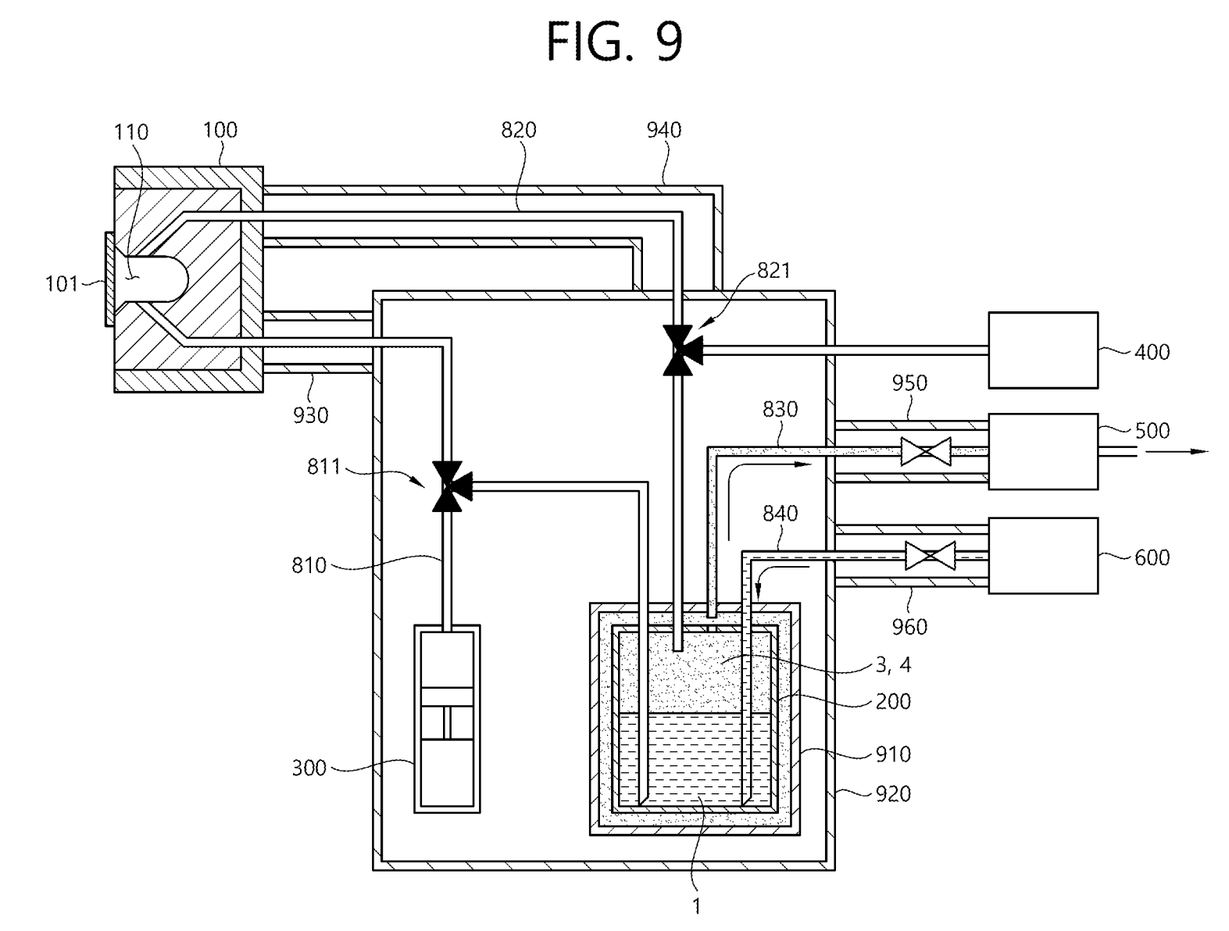
FIG. 9 illustrates a figure of moving liquefied radium before performing a reloading step.

FIG. 9 illustrates a figure of moving liquefied radium before performing a reloading step.

After passing the remaining liquefied radium 1 through a refinement process such that remaining liquefied radium 1 having liquefied actinium 2 separated therefrom becomes pure liquefied radium, and concentrating liquid increased in the process of separating radium to prepare a fixed quantity of radium, the fixed quantity of radium is transferred to the vial 200 again. Thereafter, the processes can be repeatedly performed by starting a production process from the loading step. Meanwhile, the reloading process may be configured such that, when the pure liquefied radium is loaded into the vial in the reloading step, gas is discharged to the outside of the vial along a gas discharge flow path 830 according to pressure increased in a manner similar to those of the loading and unloading steps. Therefore, gas including radon may be naturally discharged even in a reloading process. Meanwhile, the pure liquefied radium can be transferred to the vial by using a helium gas during the reloading process. However, the aforementioned method of transferring the pure liquefied radium is an example only, the pure liquefied radium may be transferred by various methods in addition to a method of using the helium gas.

Hereinafter, a concept of discarding the second shielding box will be described when a radioactive liquid and a radioactive gas are deviated from a normal flow path, and are flown out to the inside of the second shielding box. The liquid and gas may be flown out of the normal flow path when a portion of the flow path is damaged, or elements provided inside the second shielding box are damaged during using of an apparatus for producing a nuclide. Since a half-life of particularly radium among radioactive materials is turned out to be 1,602 years, and complete decontamination is also difficult, it is difficult to secure stability during repairing of an apparatus. Therefore, the apparatus can be repaired while preventing external contamination by discharging the second shielding box after entirely sealing a second shielding box although a radioactive liquid is flown out in the present disclosure.

Figure 10:
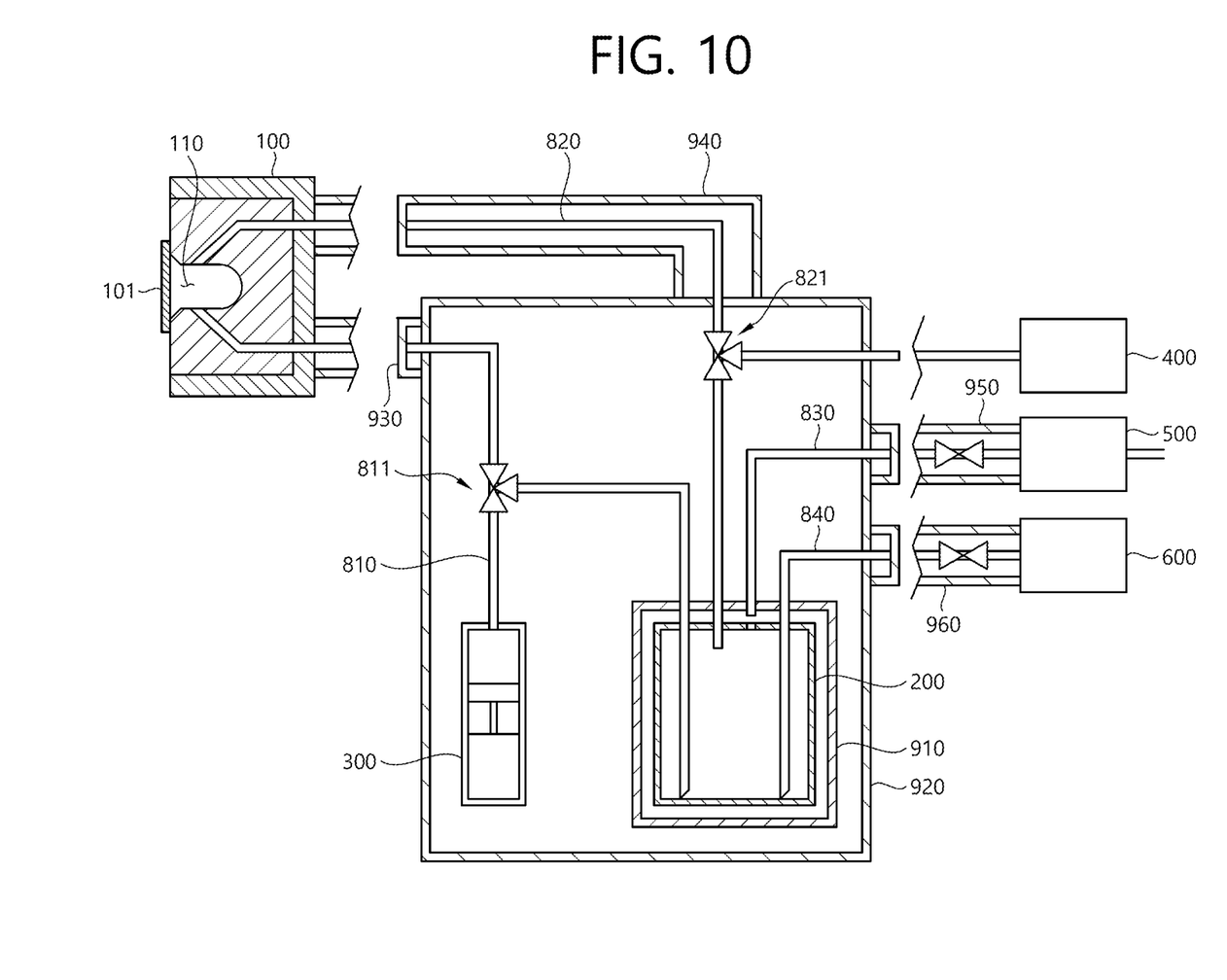
FIG. 10 illustrates a concept of sealing the second shielding box to discard a second shielding box in FIG. 2.

FIG. 10 illustrates a concept of sealing the second shielding box to discard a second shielding box in FIG. 2.

As illustrated in FIG. 10, the flow paths and shielding pipes can be discarded along with elements provided inside the second shielding box 920 after cutting and sealing all flow paths connected to the second shielding box, and sealing and cutting a first shielding pipe 930, a second shielding pipe 940, a third shielding pipe 950 and a fourth shielding pipe 960 when outflow of a radioactive material (radium 2 or radon 3) occurs inside a second shielding box 920. Eventually, although the radioactive material is flown out, an element capable of additionally shielding the radioactive material is provided to be able to prevent a contaminated zone from being expanded. Thereafter, a contaminated second shielding box 920 is sealed and discarded, the contaminated second shielding box 920 can be replaced with a component including a new second shielding box 920, and operator exposure to radiation can be prevented even during a replacement operation.

Meanwhile, it can be determined that outflow of the radioactive material has been occurred when pressure is lowered to a predetermined level or less and is not recovered by allowing a control unit to monitor pressure sensor values in an apparatus for producing a nuclide.

Figure 11:
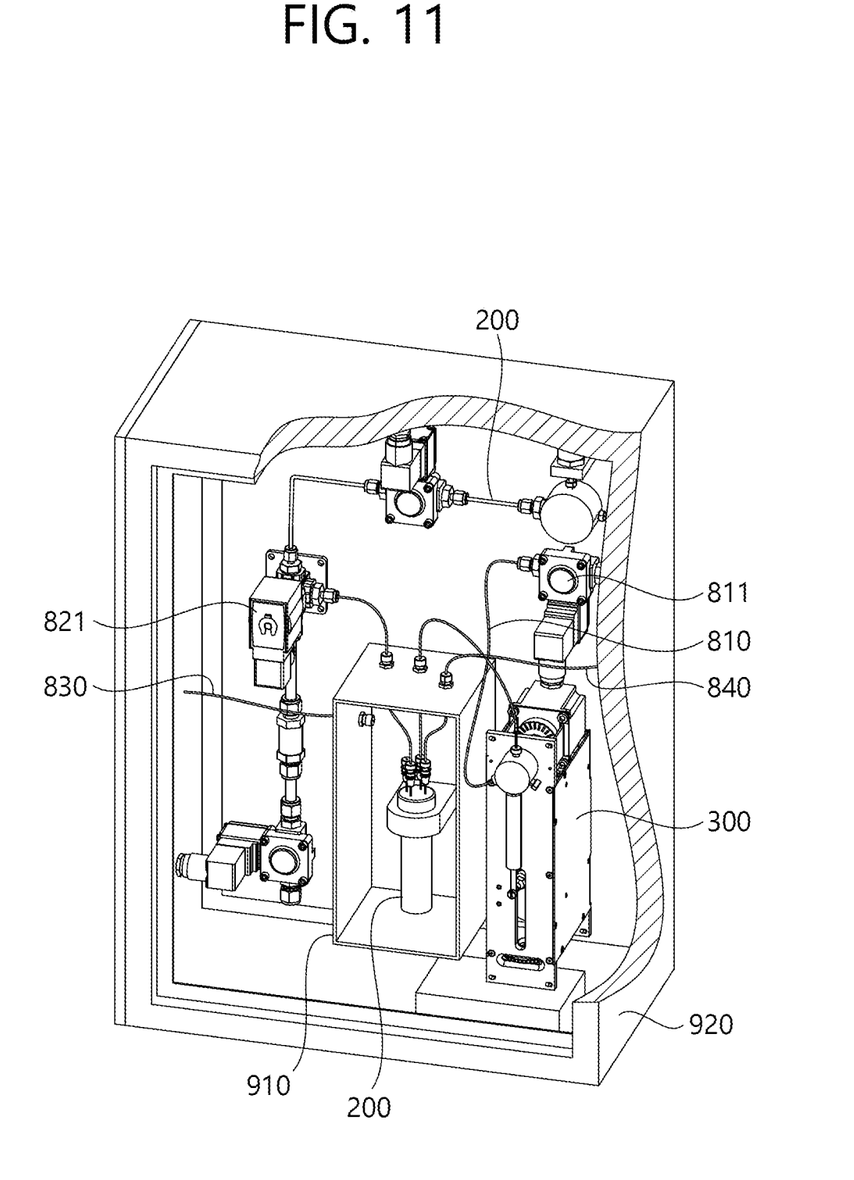
FIG. 11 is a sectional perspective view illustrating configuration of the second shielding box and its interior in an embodiment according to the present disclosure.

FIG. 11 is a sectional perspective view illustrating configuration of the second shielding box and its interior in an embodiment according to the present disclosure.

A first shielding box 910 and a second shielding box 920 of a radioactive gas shielding unit 900 are formed in a rectangular parallelepiped shape, and may be configured such that walls of the first shielding box 910 and the second shielding box 920 each have a predetermined thickness. The second shielding box 920 is configured such that other elements can be fixed to one inner surface of the second shielding box 920. FIG. 11 discloses a configuration in which the first shielding box 910, a syringe pump 300, a portion of a first flow path 810, a portion of a second flow path 820, a first 3-way valve 811 and a second 3-way valve 821 are fixed to an inner wall of one inner side of the second shielding box 920.

The first shielding box 910 is configured such that a vial 200 may be provided inside the first shielding box 910, and the first flow path 810, the second flow path 820 and a product transfer flow path 840 may be connected to the first shielding box 910 while passing through one side wall of the first shielding box 910 as described above. A gas discharge flow path 830 is connected to one side of the first shielding box 910 and is configured such that gas discharged from the vial 200 can be naturally discharged to the gas discharge flow path when pressure within the first shielding box 910 is increased.

The apparatus can prevent a radioactive gas from being diffused to the outside when a radioactive gas is flown out from the inside of the first shielding box 910 while using an apparatus for producing a nuclide according to the present disclosure, specifically when outflow of the radioactive gas occurs, or a radioactive liquid material is flown out such that the radioactive gas is generated from the radioactive liquid material. When the radioactive gas is flown out, a plurality of shielding pipes connected to the second shielding box 920 are sealed, and the second shielding box 920 itself may be discarded.

As illustrate above, an apparatus for producing a nuclide by using a liquid target according to the present disclosure can minimize loss of a reactant by performing a nuclear reaction process using a target of a liquefied state and reusing a liquefied target on which the nuclear reaction process has not been performed, and can improve safety by enabling a radioactive gas generated to be disposed.

What is claimed is:

1. An apparatus for producing a nuclide by using a liquid reactant, the apparatus including:
   a chamber provided with a reaction space which is configured to accommodate the liquid reactant;

a vial connected to the chamber, the vial configured to supply the liquid reactant to the chamber before a nuclear reaction process and receive a liquid product from the chamber after the nuclear reaction process;

a syringe pump connected between the chamber and the vial, the syringe pump configured to drive the liquid reactant from the vial to the chamber;

a trap connected to the vial and configured to collect radioactive gas from the vial; and a first flow path connecting a lower side of the reaction space with the syringe pump and the vial, the first flow path including a branched section having a first 3-way valve configured to select a transfer path of the liquid reactant, the liquid product, and/or the radioactive gas along the first flow path.

2. The apparatus of claim 1, wherein the liquid reactant comprises liquefied radium (Ra-226), the liquid product comprises liquefied radium (Ra-226) and liquefied actinium (Ac-225), and the radioactive gas is radon (Rn).

3. The apparatus of claim 2, additionally including a first shielding box surrounding the vial and configured to confine the radioactive gas.

4. The apparatus of claim 3, additionally including a second shielding box surrounding the syringe pump and the first shielding box and configured to prevent leakage of the radioactive gas to an exterior of the second shielding box.

5. The apparatus of claim 4, additionally including an inert gas source configured to supply an inert gas to the chamber and transfer the liquid product from the chamber to the vial.

6. The apparatus of claim 5, additionally including:
a second flow path connecting an upper side of the reaction space with the vial and the inert gas source, the second flow path including a branched section having a second 3-way valve configured to select a transfer path of the inert gas, and/or the radioactive gas along the second flow path.

7. The apparatus of claim 6, wherein the branched section of the first flow path, the first 3-way valve, the branched section of the second flow path, and the second 3-way valve are disposed inside the second shielding box.

8. The apparatus of claim 7, additionally including:
a first shielding pipe surrounding a portion of the first flow path positioned between the second shielding box and the chamber; and
a second shielding pipe surrounding a portion of the second flow path positioned between the second shielding box and the chamber.

9. The apparatus of claim 6, wherein, when loading the liquid reactant into the chamber the first 3-way valve provides a liquid reactant transfer path along a first portion of the first flow path from the vial to the syringe pump and along a second portion of the first flow path from the syringe pump to the lower side of the reaction space, and the second 3-way valve provides a radioactive gas transfer path along the second flow path from the chamber to the vial as the liquid reactant is transferred to the chamber.

10. The apparatus of claim 6, wherein, when unloading the liquid product after the nuclear reaction process, the second 3-way valve provides the inert gas to the chamber from the inert gas source, and the first 3-way valve provides a liquid product transfer path along the first flow path from the chamber to the vial and a gas transfer path from the chamber to the vial.

* * * * *